US008563288B2

(12) United States Patent
Nur et al.

(10) Patent No.: US 8,563,288 B2
(45) Date of Patent: *Oct. 22, 2013

(54) REMOVAL OF PLASMIN OR PLASMINOGEN FROM CRYOPRECIPITATE (75) Inventors: Israel Nur, Timorim (IL); Liliana Bar, Rehovot (IL); Malkit Azachi, Rehovot (IL)

(73) Assignee: Omrix Biopharmaceuticals Inc., Fairfax, VA (US)

(*) Notice: Subject to any disclaimer, the term of this patent is extended or adjusted under 35 U.S.C. 154(b) by 774 days.

This patent is subject to a terminal disclaimer.

(21) Appl. No.: 12/289,499

(22) Filed: Oct. 29, 2008

(65) Prior Publication Data
US 2009/0176293 A1 Jul. 9, 2009

Related U.S. Application Data (60) Division of application No. 11/581,753, filed on Oct. 17, 2006, now Pat. No. 7,641,918, which is a continuation of application No. 10/150,490, filed on May 20, 2002, now Pat. No. 7,125,569.

(60) Provisional application No. 60/291,968, filed on May 21, 2001.

(30) Foreign Application Priority Data

Jun. 21, 2001 (EP) .................................... 01115157

(51) Int. Cl.
C12N 9/66 (2006.01)
A61K 35/16 (2006.01)
(52) U.S. Cl.
USPC .......................................... 435/217; 424/530
(58) Field of Classification Search
None
See application file for complete search history.

(56) References Cited

U.S. PATENT DOCUMENTS

| 3,943,245 | A | 3/1976 | Silverstein |
| 4,639,513 | A | 1/1987 | Hou et al. |
| 5,362,859 | A | 11/1994 | Zale |
| 5,792,835 | A | 8/1998 | Tse et al. |
| 6,451,978 | B2 | 9/2002 | Winge |
| 7,125,569 | B2 * | 10/2006 | Nur et al. ...................... 424/530 |

FOREIGN PATENT DOCUMENTS

| EP | 0467932 | 1/1992 |
| JP | 63091080 | 4/1988 |
| JP | 8225461 | 9/1996 |
| JP | 9077726 | 3/1997 |
| SU | 979508 A1 | 12/1982 |
| SU | 1727839 A1 | 4/1992 |
| WO | WO 90/09238 | 8/1990 |
| WO | WO 9012091 | 10/1990 |
| WO | WO 94/00483 | 1/1994 |
| WO | WO 02/095019 | 11/2002 |

OTHER PUBLICATIONS

Petros et al., "Proton NMR Studies of Aliphatic Ligand Binding to Human Plasminogen Kringle 4", Biochemistry 28 : 1368-1376 (1989).*
Moroz et al., "Fibrinolysis in Normal Plasma and Blood: Evidence for Significant Mechanisms Independent of the Plasminogen-Plasim System", Blood, vol. 48, No. 4 Oct. 1976, pp. 531-545, XP-001029014.
Plow, et al., Immunochemical Characterization of a Low Affinity Lysine Binding Site within Plasminogen, The Journal of Biological Chemistry, 256, 10864-10869, 1981.
Ravon et al. "Monoclonal antibody F1 binds to the kringle domain of factor XII and induces enhanced susceptibility for cleavage by kallikrein." Blood, 1995 86: 4134-4143.
Keesler et al. "The binding activity of the macrophage lipoprotein (a)/ Apolipoprotein (a) receptor is induced by cholesterol via a post-translational mechanism and recognizes distinct kringle domains on apolipoprotein (a)." The Journal of Biological Chemistry, vol. 271, No. 50, Dec. 13, 1996, pp. 32096-32104.
Cao et al. "Kringle domains of human angiostatin." The Journal of Biological Chemistry, vol. 271, No. 46, Nov. 15, 1996, pp. 29461-29467.
Holland et al. Deriving the generic structure of the fibronectin type II domain from the prothrombin Kringle 1 crystal structure.: The EMBO Journal, vol. 6, No. 7, pp. 1875-1880, 1987.
Ozhogina et al. "Origin of fibronectin type II (FN2) modules: Structural analyses of distantly-related members of the kringle family identify the kringle domain of neurotrypsin as a potential link between FN2 domains and kringles." Protein Science (2001), 10: 2114-2122.
Petros et al. "$^1$H NMR studies of aliphatic ligand binding to human plasminogen kringle 4." Biochemistry 1989, 28, 1368-1376.
McRoyan et al., "Antithrombin III, plasminogen, plasmin, and alpha-s-antiplasmin in donor blood and plasma components", Annals of Clinical and Laboratory Science 15 (2): 165-170 (1985).
Fu et al., "Sequential purification of human apolipoprotein B-100. albumin, and fibrinogen by immunoaffinity chromatography", Analytical Biochemistry 247 (2): 228-236 (1997).
Burnouf-Radosevich et al., "Chromatographic preparation of a therapeutic highly purified von Willebrand factor concentrate from human cryoprecipitate", Vox Sanguinis 62 (1): 1-11 (1992).
Liu et al., "Preparation of highly purified fribrinogen free from plasminogen", Xi'an Yike Daxue Xuebao 17 (3): 395-387 (1996).

(Continued)

*Primary Examiner* — Sandra Saucier
(74) *Attorney, Agent, or Firm* — Jacobson Holman, PLLC (57) ABSTRACT

A method for specifically removing or isolating plasmin(ogen) or plasmin in presence of fibrinogen from a mixture containing plasmin(ogen) or plasmin by contacting the mixture with a rigid amino acid wherein the amino group of the amino acid and the carboxylic group of the amino acid are about 6-8 Angstroms, preferably about 7 Angstroms apart and the rigid amino acid is covalently bound to the support via the amino group of the amino acid.

16 Claims, 1 Drawing Sheet

(56) References Cited

OTHER PUBLICATIONS

Poullouin et al., "Plasma Fibronectin: Three Steps to Purification and Stability", Protein Expression and Purification 17 (1): 146-152 (1999).
Peng et al., "Isolation and purificaiton of human serum alpha 1-antitrypsin and the preparation of its antiserum", Shengwu Huaxue Yu Shengwu Wuli Jinzhan 45: 59-62 (1982).
Weinstein, M.J. et al 'Differential Specifities of the Thrombin, Plasmin and Trypsin with regard to Synthetic and Natural Substrates and Inhibitors' RF Biochim Biophys Acta (1972) vol. 258 pp. 577-590.
Chen, Z.L. et al 'Neuronal death in the hippocampus is promoted by Plasmincatalyzed Degradation of Liminin,' Cell (1997) vol. 91 pp. 917-925.
Ling, C.M. et al 'Mechanism of Formation of Bovine Plasmin(ogen) Activator from Human Plasmin' J. Biol Chem. (1965) vol. 240 pp. 4212-4218.
Fischer M.B. et al 'Binding of Disease Associated Prion Protein to Plasmin(ogen)' Nature (2000) vol. 408 pp. 479-483.
Alkjaersig N., The purification and properties of human plasmin(ogen). Biochem. J. 1963, 93:171-182.
Deutsch and Meltz. Science (1997) vol. 170 pp. 1095-1096.
Schreiber, A.D. et al 'Plasma Inhibitors of the Components of the Fibrinolytic Pathway in Man' J. Clin. Invest. vol. 52 (1973) pp. 1394-1401.
Fredenburgh, J.P. et al 'Lysplasmin(ogen) is a Significant Intermediate in the Activation of Gluplasmin(ogen) during Fibrinolysis In Vitro' J. Biol. Chem. vol. 267 (1992) pp. 26150-26156.
Miyashita, C. et al 'Plasmin(ogen): A Brief Introduction into ist Biochemistry and Function' Haemostasis vol. 1 (1988) pp. 7-13.
Bradford, MM 'A Rapid and Sensitive Method for the Quantitation of Microgram Quantities of Protein Utilizing the Principle of Protein-Dye Binding,' Anal Biochem. vol. 72 (1976) pp. 248-254.
Robbins, K.C. et al 'Plasmin(ogen) and Plasmin,' Methods Enzymol. vol. 45 (1976) pp. 257-273.
Hatton et al. "The relevance of the structure of lysine bound to Sepharose for the affinity of rabbit plasminogen", Biochim. Biophys. Acta., 379(2), 1975, 504-11.
Westlund et al. "Effect of EACA, PAMBA, AMCA and AMBOCA on Fibrinolysis Induced by Streptokinase, Uroklnase and Tissue Activator," Haemostasis 11: (1982) 235-241.
Mathews et al. "Crystal Structures of the Recombinant Kringle 1 Domain of Human Plasminogen in Complexes with the Ligands ε-Aminocaproic Acid and *trans*-4- (Aminomethyl) cyclohexane-1-carboxylic Acid," Biochemistry, 35, 1996, 2567-2276.
Markwardt "Fibrinolytics and Antifibrinolytics," Annals of Internal Medicine, 91: (1979) 670.
Shimura et al "High-Performance Affinity Chromatography of Plasmin and Plasminogen on a Hydrophilic Vinyl-Polymer Gel Coupled with p-Aminobenzamidine," Journal of Chromatography, 292: (1984) 369-382.
Iwamoto "Plasminogen-Plasmin System IX. Specific Binding of Tranexaminc Acid to Plasmin" Thrombos. Diathes. Haemorrh, 33: (1975) 573-585.
Masahiro Iwamoto, "Pasminogen—Plasmin System IX. Specific Binding of Tranexamic Acid to Plasmin" 1975, pp. 573-585, XP-001021276.
Leonard A. Moroz et al., "Fibrinolysis in Normal Plasma and Blood: Evidence for Significant Mechanisms Independent of the Plasminogen-Plasmin System", Blood, vol. 48, No. 4 Oct. 1976, pp. 531-545, XP-001029014.

\* cited by examiner

REMOVAL OF PLASMIN OR PLASMINOGEN FROM CRYOPRECIPITATE

CROSS-REFERENCE TO RELATED APPLICATIONS

This is a divisional of Ser. No. 11/581,753, filed Oct. 17, 2006 now U.S. Pat. No. 7,641,918, which is a continuation of Ser. No. 10/150,490, filed 20 May 2002 now U.S. Pat. No. 7,125,569, which claims the benefit of U.S. Provisional Application No. 60/291,968, filed 21 May 2001.

BACKGROUND OF THE INVENTION

1. Field of the Invention

The present invention relates to a resin and method for the specific removal of plasmin(ogen) and its derivatives from protein solutions, where the resulting protein solution can be used for intravenous administration and for local applications, i.e. matrix support for sustained release and healing of wounds, either as a sole active component or combined with other pharmaceutical, acceptable drugs. The removal of plasmin(ogen) would preserve the integrity and the function of the protein solution for longer incubation periods. This invention is also related to the production of highly purified plasmin(ogen) for therapeutic use.

2. Related Art

Plasminogen or its active molecule plasmin (in the following plasmin(ogen)), very frequently contaminates protein solutions, especially those extracted from animal fluids or animal organs. The presence of plasmin(ogen) in a protein solution presents a multiple threat to its acceptance as a stable pharmaceutical product, due to the molecule's known proteolytic activity on various protein and peptides at arginyl and lysyl peptide bonds (Weinstein M. J., Doolittle R F. Differential specificities of the thrombin, plasmin and trypsin with regard to synthetic and natural substrates and inhibitors RF Biochim Biopliys Acta. 1972 258:577-90 and Ling C M, Summaria L, Robbins K C. Mechanism of formation of bovine plasmin(ogen) activator from human plasmin. J Biol chem. 1965. 240:4212-B); and basic amino acids, its stimulatory activity on various tissues, especially the central nerve tissue and its role in binding (Chen Z L, Strickland S Neuronal death in the hippocampus is promoted by plasmincatalyzed degradation of liminin. Cell. 1997. 91:917-25) and probably carrying prions in the blood of mammals Fischer (MB, Roeckl C, Parizek P, Schwarz H P. Aguzzi A Binding of disease associated prion protein to plasmin(ogen). Nature. 2000. 408:479-83).

Several chromatographic methods were developed for the purification of plasmin(ogen) from protein solutions and hence, removing plasmin(ogen) from protein solution.

These methods are essentially based on two principles. The first group is based on several consecutive purification steps that utilize the differential solubility, isoelectric point, or molecular size distribution Alkjaerisig N. (The purification and properties of human plasmin(ogen). Biochem. J. 1963, 93:171-182). Since their prime target was to purify plasmin(ogen), these methods totally distorted the composition of the protein solution. The second group of methods is based on one step affinity purification. The purification is based on binding plasmin(ogen) to various synthetic ω-amino carboxylic acid ligands that can bind onto the lysine binding sites on the plasmin(ogen) heavy chain. These sites, consist of 5 triple loop disulfide bridges with internal sequence homology known as the plasmin(ogen) kringles, located on the $NH_2$ plasmin(ogen) heavy chain and far from the catalytic site located on the COOH light chain, bind fibrin(ogen). Another possibility for affinity chromatography is to bind plasmin(ogen) via the catalytic site, a potentially less specific binding since it may bind many proteins such as serine proteases having similar or lower affinity to arginyl and lysyl peptide bonds and basic amino acids. In summary, it might be concluded that in general, plasmin(ogen) affinity chromatography is performed by a given ligand that chemically and ionically resembles ω-amino-carboxylic acid or the substrate of the plasmin catalytic site. The ligand is bound to the resin through an adequate spacer or linker. However an ideal affinity resin for the removal of plasmin(ogen) is not essentially the same resin found ideal for the purification of plasmin(ogen). Such resins should contain a ligand that binds plasmin(ogen) at high affinity and has very low affinity to other proteins such as other serine proteases and especially very low affinity for fibrinogen which is the main protein in Plasma Cohn's fraction I or in cryoprecipitate. It is also important that the removal of plasmin(ogen) by using the given affinity chromatography might be performed in a wide range of buffers and not be restricted to a certain buffer that may endanger the stability and the integrity of proteins in the solution, those being a main concern and not the plasmin(ogen).

The antifibrinolytic potency (ability to inhibit the binding of plasmin(ogen) to fibrinogen at high affinity) of the ω-amino-carboxylic acids depends on the presence of free amino and carboxylic group and on the distance between the COOH-group and the carbon atoms to which the $NH_2$-group is attached (Markwardt 1978) such as ϵ-amino caproic acid (EACA), and p-amino benzamidine (PAMBA). Comparison between the antifibrinolytic activities of EACA and PAMBA showed that the latter is about three times more active. Shimura et al (1984) designed a resin in which p-amino benzamidine was bound to microparticles of hydrophilic vinyl polymer via a spacer (linker) moiety. By using this resin, Shimura et al were able to separate plasmin and plasminogen by high performance affinity chromatography. The facts that plasmin(ogen) could not be eluted by 6-aminohexanoic acid alone and that 3 M urea had to be included in the elution buffer indicated a two-site interaction of plasmin with this immobilized ligand i.e., the lysine-binding sites on the heavy chain and the catalytic site on the light chain. This may explain the finding by other researchers that p-amino benzamidine removes also some other proteins.

Another resin, the lysine-resin, is manufactured and used for the affinity purification of plasmin(ogen). However, the antifibrinolytic potency of lysine is very low and thus, also its binding affinity. It also binds to other proteins and its specificityis buffer dependent.

Moroz L A. Gilmore N J Fibrinolysis in normal plasma and blood: evidence for significant mechanisms independent of the plasminogen-plasmin system, Blood, 1976, 48, 531-45 disclose a preparation of plasmin(ogen)-free plasma by affinity chromatography. Based on the methods employed the authors report about observations indicating that processes which culminate in the generation of the fibrinolytic enzyme plasmin play at most a minor role in the spontaneous or basal fibrinolytic activity measurable in normal human plasma. Tranexamic acid was used together with other protease inhibitors as plasmin inhibitors for measuring fibrinolytic activity. For preparation of the plasmin(ogen)-free plasma the method of Deutsch and Meltz, Science 170; 1095-1096, 1997 was employed.

Iwamoto in Thrombos. Diathes. Heamorrh. (Stuttg.), 1975, 33, 573 discloses specific binding of a tranexamic acid to plasmin. Although tranexamic acid is identified as a powerful ligand of plasmin, it is indicated that the anti-fibrinolytic effect of tranexamic acid is a result of not only the binding to plasmin(ogen), but also of the enhancement of cooperation of the natural antiplasmins. Therefore one would conclude that binding of tranexamic acid to a solid support will not only remove plasmin(ogen) from plasma but also the natural antiplasmins. One would also suggest that tranexamic acids may cause of formation of aggregates (conglomerates) with plasmin inhibitors. This understanding is based on the discrepancy, which can be found when comparing the anti-fibrinolytic activity of ε-amino-caproic acid and tranexamic acid resulting in 98 and 91% inhibition in urokinase-stimulated plasma versus plasma that has been heparinized oral blood (65 and 39% for ε-amino-caproic acid and tranexamic acid respectively—cf. tables 2 and 7 in the Moroz et al. paper). One would expect that due to their high binding ratio tranexamic acid and ε-amino-caproic acid are good candidates for high affinity ligands. However, one would also expect this ligands would block an affinity column as a result binding of plasmin and plasmin inhibitor complexes.

SUMMARY OF THE INVENTION

The present invention is based upon the result that a rigid amino acid was surprisingly found as to be able for specifically binding plasmin(ogen). "Specifically binding" within the context of the description of the invention means that out of a mixture containing proteins, such as plasmin(ogen) and fibrinogen essentially the plasmin(ogen) is removed from the mixture whereas fibrinogen is maintained almost unaffected in the mixture. Preferably at least 85 to 99% of the plasmin(ogen) is removed and at least 85% of fibrinogen remains in the mixture. More preferably plasmin(ogen) is removed to at least 98.0% to 99.9% or fibrinogen remains 95% by 99%.

The amino group of the amino acid and the carboxylic group of the amino acid are about 6-8 Angstroms, preferably about 7 Angstroms apart and the rigid amino acid is covalently bound to a support via the amino group of the amino acid. In particular preferred are tranexamic acid in its transconfiguration and 4-aminomethylbicyclo-[2.2.2.]-octane-1-carboxylic acid (EMBOCA).

It was surprisingly found that in the first place ε-amino-caproic acid did not work as well as tranexamic acid and that once the tranexamic acid is bound to a solid surface it looses all its extra plasmin(ogen) binding capacity (so-called cooperation) and the resin removes only plasmin(ogen) from plasma or plasma products. If ε-amino-caproic acid is attached to the column its extra plasmin(ogen) activity still remains and still binds fibrinogen and other proteins from plasma, whereas the extra plasmin(ogen) activity of tranexamic acid according to the invention is totally abolished. However, the affinity of the tranexamic acid resin to plasmin(ogen) is not affected.

The rigid amino acid is attached to an appropriate spacer, in particular longer than 3 carbon atoms, and the support and the affinity material may deplete plasmin(ogen) from a mixture containing proteins without further altering the protein solution composition. The removal can be done in presence of various buffers. The method of the invention is also suitable for making pure fractions of plasmin(ogen) after elution from the affinity support.

DETAILED DESCRIPTION OF THE INVENTION

The invention pertains to a method for specifically removing or isolating plasmin(ogen) in presence of fibrinogen from a mixture containing plasmin(ogen) by contacting the mixture with a rigid amino acid wherein the amino group of the amino acid and the carboxylic group of the amino acid are about 6-8 Angstroms, preferably about 7 Angstroms apart and the rigid amino acid is covalently bound to the support via the amino group of the amino acid.

Preferably, in the method according to the invention the mixture is selected from the group consisting of body fluids such as blood; blood fractions, cryoprecipitate, cell cultures, animal tissue extracts, such as bovine lungs, bovine intestines or animal bone extracts gelatin, bovine serum albumin as well as animal derived water immiscible fats, such as lanoline (PC-phosphatidyl choline).

The method of the invention can be used to obtain highly purified plasmin(ogen) from the respective mixtures. After contacting the mixture with e.g. a chromatographic material having bound the rigid amino acid, the plasmin(ogen) can be eluted from the solid affinity material. The, as such known, principles of solid phase extraction can be applied here as well. The plasmin(ogen) can be eluted by a solution containing a ligand, which competes with binding sites of the rigid amino acid, e.g. tranexamic acid, at the plasmin(ogen) protein. Such ligands are typically ε-aminoacids, preferably lysine. For example, lysine may be employed in concentrations of 0.85% by weight to 0.99% by weight. Also other concentrations are possible, especially when the ionic strength of the elution medium is balanced by other ingredients e.g. electrolytes.

The plasmin(ogen) eluting from the solid phase can be made free of the elution buffer by a method, which extracts the buffer components for example dialysis. The plasmin(ogen) obtainable according to the method of the invention is characterized by very high purity. The unique property becomes evident from the data:

SUMMARY TABLE 1

Comparison of specific activity, purification factor and recovery of plasmin(ogen) from cryo-depleted FFP plasma using the preferred loading and elution conditions for each of the resins.

| Resin used | Method | Specific activity (mg plasmin(ogen)/mg protein) | Purification factor | Recovery (%) |
|---|---|---|---|---|
| TEA-Sepharose 4B | 2 | 0.794 | 567 | 91.6 |
| Lysine-Ceramic Hyper DF | 2 | 0.444 | 444 | 10.9 |
| Lysine-Sepharose 4B | 1 | 0.121 | 101 | 11.6 |

SUMMARY TABLE 2

Comparison of plasmin(ogen) removal from cryo-depleted FFP plasma using the preferred loading conditions for each resin.

| Resin used | Method | Removal (%) |
|---|---|---|
| TEA-Sepharose 4B | 1 and 2* | 99.5 |
| Lysine-Ceramic Hyper DF | 1 | 54.6 |
| Lysine-Sepharose 4B | 1 | 58.0 |

*Both methods are identical up to and including collection of the unbound peak.

As can be seen from the summary table, when commercially available resins with immobilized-Lysine ligands and the TEA resin were used under optimized chromatographic conditions, the recovery and specific activity of the plasmin(ogen) were higher with the TEA resin (summary table 1). It is also note worthy that the TEA resin is much more efficient in removing plasmin(ogen) (as indicated by the test for Gluplasmin(ogen)) from the cryo-depleted plasma, than the lysine resin (summary table 2).

The purity of the eluates was assessed by SDS-gel electrophoresis. The eluates of the three different resins (TEA-Sepharose, Lys-Ceramic Hyper DF and Lys-Sepharose 4B) underwent SDS-PAG by loading a 5-12% gradient of acrylamide and loading 7 μg protein per lane. The resulting Coomassie Blue stained gel is showed in FIG. 1.

Figure 1:
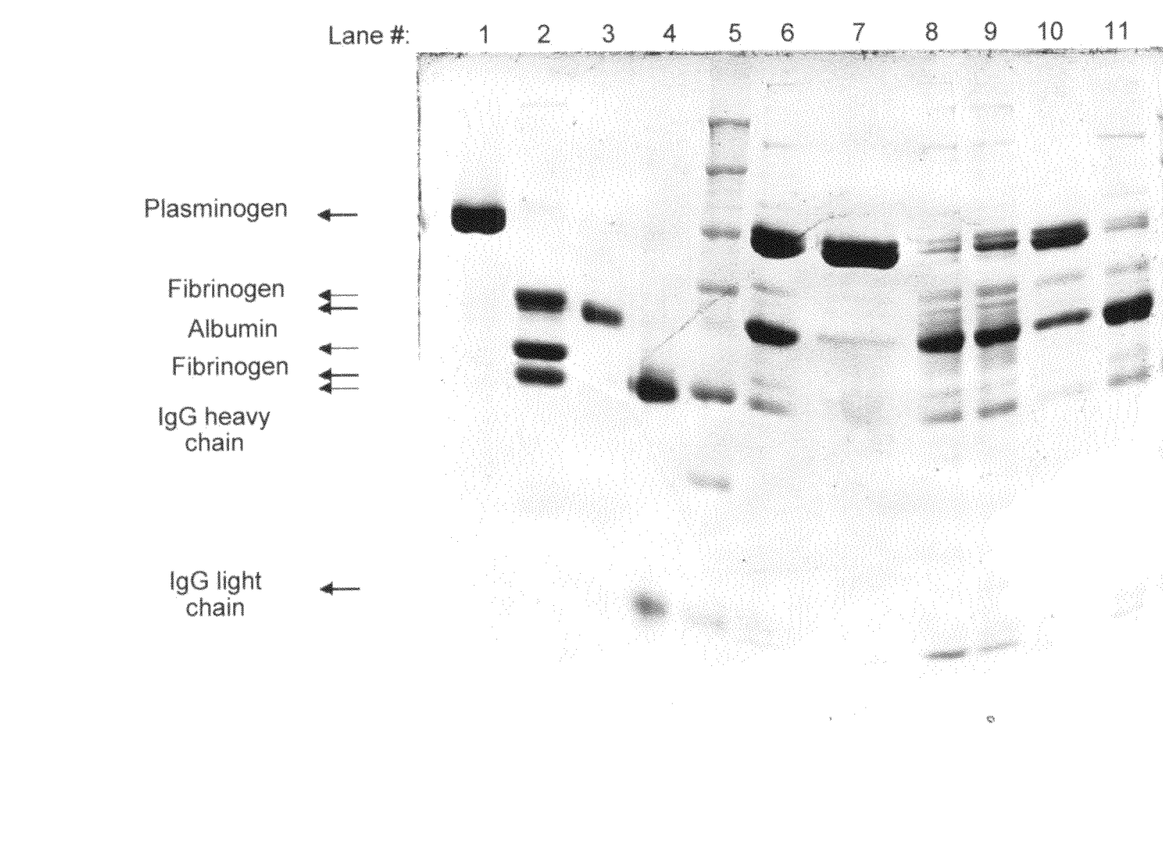
FIG. 1 shows a gradient gel SDS-PAGE (5-12% polyacrylamide) of 7 μg of proteins eluted by the two methods (described in the material and method), with three different resins -TEA-Sepharose, Lys-Ceramic Hyper DF and Lys-Sepharose 4B. Lanes 1—Glu plasminogen; 2—fibrinogen; 3—Albumin; 4—Immunoglobulin G; 5—molecular wt. marker; Elution peaks of: 6—TEA using method; 7—TAE using method 2; 8—Lysine Ceramic Hyper D by method 1; 9—Lysine Sepharose by method 1; 10—Lysine Ceramic Hyper D by method 1; 11—Lysine Sepharose by method 1.

FIG. 1 shows a gradient gel SDS-PAGE (5-12% polyacrylamide) of 7 μg of proteins eluted by the two methods (described in the material and method), with three different resins -TEA-Sepharose, Lys-Ceramic Hyper DF and Lys-Sepharose 4B. Lanes 1—Glu plasminogen; 2—fibrinogen; 3—Albumin; 4—Immunoglobulin G; 5—molecular wt. marker; Elution peaks of: 6—TEA using method; 7—TAE using method 2; 8—Lysine Ceramic Hyper D by method 1; 9—Lysine Sepharose by method 1; 10—Lysine Ceramic Hyper D by method 1; 11—Lysine Sepharose by method 1.

The resulting protein bands and the purity of the product correlate well with the specific activity of the plasmin(ogen) as indicated in summary table 1. This indicates that the use of the TEA-Sepharose resin resulted in a highly purified plasmin(ogen) with only minor contamination with albumin. It seems that no further purification is needed to use this product for the clinical indications.

Therefore a plasmin(ogen) containing composition is also subject matter of the present invention.

Subject of the present invention is also a support having covalently bound a rigid amino acid wherein the amino group of the amino acid and the carboxylic group of the amino acid are apart about 6-8 Angstroms, preferably about 7 Angstroms.

The support for performing the method of the invention is preferably a chromatographic material which is able to bind a rigid amino acid wherein the amino group of the amino acid and the carboxylic group of the amino acid are apart about 6-8 Angstroms, preferably about 7 Angstroms. The distance between the amino group and the carboxylic group is kept substantially constant by the rigid constitution of the amino acid. The rigidity of the amino acid can be generated by alicyclic rings, preferably by a cyclohexan ring, wherein the amino and carboxyl group are arranged in 1,4 position of the alicyclic ring. Also aromatic systems, e.g. substituted benzoic acids or aniline substituted acetic acid are within the scope of the invention.

According to the invention the support preferably has bound amino acids selected from the group consisting of tranexamic acid and EMBOCA.

The chromatographic material to be employed according to the method of the invention is e.g. a hydrophilic material such as agarose, cellulose, controlled pore glass, silica gels, dextranes or an organic artificial polymer such as based on polyacrylamides polystyrens. Typical materials are commercially available under the trade names Sephacryl® (Pharmacia, Sweden), Ultragel® (Biosepara, France) TSK-Gel Toyopearl® (Toso Corp., Japan), HEMA (Alltech Ass. (Deerfield, II, USA), Eupergit® (Rohm Pharma, Darmstadt, Germany). Also materials based on azlactones (3M, St. Paul, Minn., USA) can be used. Particularly preferred is Agarose® or Sepharose®. These materials are commercially available for example from Sigma, St. Louis.

In a preferred embodiment, the method according to the invention is performed by employing a particulate chromatographic material or a monolithic block-material. The particulate material can be suspended in an appropriate medium and the resulting slurry can be used e.g. in a chromatographic column. However, the method of the invention can also be performed in a batch. Furthermore, the polymers may be used as particulate material or also in form of membranes.

The tranexamic acid is bound to the support preferably via a linker, in particular a bifunctional linker, between the support and tranexamic acid. If a bifunctional linker is used, it can be selected from the group consisting of N-hydroxy succinimide, DAPA, CNBr, epoxy, diaminodipropylamine (DADPA), 1,6 diaminohexane, succinic acid, 1,3 diamino-2-propanol, ethylendiamine (EDA), TNB, pyridyldisulfide, iodoacetamide, maleimide activated support or combinations thereof.

The support for performing the method of the invention is preferably modified by a moiety which reacts with primary or secondary amino groups.

According to the method of the invention the mixture is incubated with the support for a sufficient time period, and eluted with a neutral aqueous solution containing sodium salts, calcium salts, buffer salts after contacting the mixture with the support having bound tranexamic acid. Subsequently, the plasmin or plasminogen may be eluted with an aqueous solution containing a sufficient amount of lysine or an equivalent which competes with the covalently bound tranexamic acid.

Subject of the invention is a mixture derived from natural sources being substantially free of plasminogen and plasmin.

In particular, the mixture of the invention is blood, a blood derivative or blood fraction, cryoprecipitate.

A blood derivative of the invention is in particular a plasma derived blood clotting factor or mixture of blood clotting factors, such as FVIII, FIX, fibrinogen, fibronectin, $\alpha_1$-antitrypsin, anti-thrombin III, von Willebrand factor, albumin, immunoglobulin.

Further, a support having tranexamic acid covalently bound is also subject of the present invention. The support of the invention is preferably a chromatographic material, more preferred a hydrophilic chromatographic material such as dextranes or an organic artificial polymer such as mentioned above. A very preferred support is Agarose® or Sepharose® to which tranexamic acid is bound.

The chromatographic material which forms the support may be a particulate material or a monolithic block-material. The latter is described in Hermanson et al, incorporated by reference (Hermanson G T, Mallia A K and Smith P K 1992 "Immobilization Affinity Ligand Techniques" pp. 454 Academic Press, Inc. San Diego, USA).

In another preferred embodiment of the invention the tranexamic acid is bound to the support via a linker between the support and tranexamic acid. This is advantageous when the support does not have functional groups being capable to bind tranexamic acid covalently. Then the support is first functionalized and then reacted with a linker which is able to bind tranexamic acid. Spacer arms or leashes are low molecular weight molecules that are used as intermediary linkers between a support or matrix and affinity ligand which is according to the invention the amino acid having a rigid structure and the amino group about 6-7 Angstrom apart from the carboxyl group. Preferably, the spacers comprise two functional groups on both ends for easy coupling to ligand and support. The spacer is typically a hydrocarbon compound having two functional groups at its ends. One of the two ends is attached covalently to the matrix using conventional or per se known reactions. The second end is covalently linked to the ligand using another coupling procedure.

Preferably, the linker is a bifunctional linker such as N-hydroxy succinimide, DAPA, CNBr, epoxy, diaminodipropylamine (DADPA), 1,6 diaminohexane, succinic acid, 1,3 diamino-2-propanol, ethylendiamine (EDA), TNB, pyridyldisulfide, iodoacetamide, maleimide activated support or combinations thereof.

Since many functionalized supports are commercially available, it may be advantageous to start with a support which is modified by a moiety which reacts with primary or secondary amino groups.

The method of the invention is further described in greater detail using as example the preparation of a substantial plasmin(ogen) free cryoprecipitate which may be the starting material for numerous blood derived products.

The cryoprecipitate is subjected to affinity chromatography with an immobilized ligand to give an adsorbed fraction and an unadsorbed fraction. The substance, which can be eluted from the adsorbed fraction, is plasmin(ogen).

The immobilized ligand may be any analogue, which can interact with the plasmin(ogen) lysine binding sites. The process for preparation of immobilized ligands that are used according to the invention is disclosed underneath. The following examples are illustrative but not limiting.

EXAMPLE 1

Immobilization of Various ε-Amino-Carboxylic Acid Ligands

A series of ε-amino-carboxylic acid ligands in combination with various spacers in several resins were either produced or purchased (if commercially available) to evaluate the plasmin(ogen) removal from plasma derived solutions. The following table summarizes all the combinations studied (the numbers below the resins relate to the section where the synthesis for each combination is described below):

TABLE 1

| Ligand Linker | P-benzamidine | Arginine | Tranexamic acid | ε-Aminohexanoic acid | Lysine |
|---|---|---|---|---|---|
| N-hydroxy-succinic |  |  |  | Sepharose 4B (1) |  |
| DADPA | Agarose 4% (2) | Agarose 4% (3) | Agarose 4% (4) |  |  |
| CNBr |  | Sepharose 4B (5) | Sepharose 4B (6) |  |  |
| Epoxy | Sepharose 6B (10) | Sepharose 6B (7) | Sepharose 6B (8) |  | Ceramic HyperDF (9) |

(1) ε-aminohexanoic acid N-hydroxysuccinimide ester Sepharose 4B was purchased from Sigma.

(2) Manufacturing of p-aminobenzamidine- Agarose 4%

The following procedure was used for the immobilization of Diaminodipropylamine (DADPA) on Agarose 4% (Pierce), the reaction took place on an amine-terminating spacer gel that is then modified with an anhydride.
25 ml DADPA-Agarose gel was washed with purified water, and then the gel was suspended in an equal volume of purified water. The slurry mixture was stirred slowly for 1 h at room temperature, while adding to it 2.5 g succinic anhydride. At the end of the stirring, the succinylated gel was washed sequentially with purified water. 1 M NaCl and again with purified water to remove the excess of unreacted succinic acid.
A negative test with TNBS (Sigma) indicated that all amines of DADPA were successfully blocked with succinic acid.
The immobilized succinilated DADPA was washed with 250 ml of purified water, then excess water was suctioned dry to a moist cake and transferred to a 500-ml beaker. The gel was resuspended in 25 ml 0.1 M MES Buffer, pH 4.7 and stirred slowly while 0.25 g of p-aminobenzamidine (Sigma) and 0.75 g EDC (Pierce) were added. The pH of the reaction mixture was maintained at 4.7 for 1 h by adding continuously 0.5 M NaOH. The reaction mixture was then left overnight at room temperature under continuous slow mixing.
The gel was washed successively with 0.5 L of each: purified water, 0.1 M sodium acetate, pH 4.7, 0.5 M sodium bicarbonate and purified water.
Immobilized p-aminobenzamidine was stored until use in 0.02% sodium azide at 4° C.

(3) Arginine - Agarose 4%

The Arginine-Agarose 4% synthesis was preferred according to the above procedure, p-aminobenzamidine- Agarose 4% (see 2).

(4) Tranexamic acid (TEA)- Agarose 4%

The Tranexamic acid (TEA)- Agarose 4% synthesis was preferred according to the above procedure, p-aminobenzamidine- Agarose 4% (see 2).

(5) Arginine- Sepharose 4B

The following procedure was used to immobilize Arginine or Tranexamic acid on CNBr-Sepharose 4B (Pharmacia) as the spacer gel. The synthesis of the two ligands at two different concentrations (10 mmol or 0.01 mmol/ml dry gel) were similar, as mentioned in this and the next section (5-6).
2.5 g of CNBr-activated Sepharose 4B were suspended in 50 ml of 1 mM HCl. The gel was swelled for 10 min at room temperature following by 15 min washing with 500 ml of 1 mM HCl on a sintered glass filter.
Arginine was dissolved in 12.5 ml of coupling buffer, 0.1 M NaHCO₃ pH 8.3 containing 0.5 M NaCl. The coupling solution containing the ligand was mixed with the gel in a plastic tube followed by overnight rolling at 4° C.
At the end of the incubation, this mixture was washed from excess of ligand with 10 gel volumes of coupling buffer through a sintered-glass filter. The protein solution was washed with 3 cycles of 50 ml buffer at alternating pH's (0.1 M acetate buffer pH 4 containing 0.5 M NaCl followed by washing with 0.1 M Tris-HCl buffer pH 8 containing 0.5 M NaCl). The immobilized Arginine-Sepharose 4B was stored until use in 0.02% sodium azide at 4° C.

(6) Tranexamic Acid (TEA)-Sepharose 4B

This synthesis was done according to the above Arginine-Sepharose 4B procedure (see section 5).

(7) Arginine-Sepharose 6B

Arginine at two different concentrations (2 mmol or 0.2 mmol/ml dry gel) was coupled to the commercially available immobilized Epoxy Sepharose 6B (Pharmacia) as follows:
2.5 g of Epoxy-activated Sepharose 6B were suspended in 200 ml of purified water. The gel was swelled for approximately 5 min at room temperature followed by washing for 1 h with 500 ml of purified water, added in aliquots, through a sintered glass filter.
20 ml of coupling buffer (0.1 M NaHCO₃ pH 9.3 and 0.5 M NaCl) and the swelled gel were poured into two tubes containing Arginine. The mixtures were mixed in a plastic tube overnight at RT.
At the end of the incubation, this mixture was washed from excess of ligand with 5 gel volumes of coupling buffer through a sinter glass filter. The product was washed with 3 cycles of alternating pH (0.1 M acetate buffer pH 4.0 and 0.5 M NaCl buffer followed by washing with 0.1 M Tris-HCl buffer pH 8 and 0.5 M NaCl). The immobilized Arginine-Sepharose 6B was stored until use with 0.02% sodium azide at 4° C.

(8) Tranexamic Acid (TEA)-Sepharose 6B

This synthesis was preferred according to the above Arginine-Sepharose 6B procedure (see section 7).

(9) L-Lysine epoxy-activated Ceramic HyperDF Hydrogel was purchased from Sigma.

(10) P-aminobenzamidine covalently attached to Sepharose 6B was purchased from Pharmacia.

EXAMPLE 2

Screening of the Different Affinity Chromatography Resins for Plasmin(ogen) Removal Human plasma pooled cryoprecipitate containing 1 IU/ml of plasmin(ogen) and 50 mg/ml fibrinogen was used for the following study.

Aliquots of frozen cryoprecipitate were thawed at 37° C. and dialyzed against buffer BN1 (0.12 M NaCl, 10 mM Tri Na-citrate, 1 mM $CaCl_2$ at pH 7.0). This protein solution was filtered through a 5 μm depth filter to obtain a clear solution. A 5 ml syringe cylinder with a diameter of 8.36 mm was packed with 1.5 ml (wet volume) of the following affinity resins described in example 1: immobilized ε-aminohexanoic acid (Sepharose 4B using CNBr as a spacer), immobilized p-aminobenzamidine/Arginine/TEA (Agarose 4% using DADPA as a spacer), immobilized Arginine/TEA (Sepharose 4B using CNBr as a spacer), immobilized Arginine/TEA (Sepharose 6B using epoxy as a spacer) and immobilized L-Lysine (Ceramic HyperDF Hydrogel using epoxy as a spacer). The optimized gel packing procedure was as follows: the packed gel was washed with 4 volumes of i) purified water, ii) 1 M NaCl, iii) purified water, iv) TLN 0.1 buffer (Tris 0.05 M Lysine 0.02 M, 0.1 M NaCl, pH 9.0), v) TLN 1 buffer (Tris 0.05 M, Lysine 0.02 M and 1 M NaCl, pH 9.0) and vi) purified water. All samples, loading and washing buffers were applied to the syringe cylinder following a centrifugation at 1000 rpm for 1 min at 25° C. Equilibration was carried out with 4 volumes of BN1 and the pre-filtered concentrated cryoprecipitate was loaded onto the resin (2:1 v/v, respectively) this mixture was then incubated for 1 h at room temperature. Aliquots of the unbound "spin" washes were collected in plastic tubes after each centrifugation. The resin was washed with at least 13 column volumes of either BN1 buffer until the $O.D_{280}$ reached to 0.02. Elution of plasmin(ogen) was carried out with TLN 1 buffer following by washing with four bed volumes of 3 M NaCl. The mini columns were tightly closed and stored at 4° C.

Resins, which degraded during the process or removed less than 50% of the plasmin(ogen) were excluded early from the study. The results are summarized in Table 2.

TABLE 2

Plasmin(ogen)P removal in the unbound material using different immobilized ligands with BN1 buffer.

| Immobilized Ligands | Removal of plasmin(ogen) (%) |
|---|---|
| ε-Aminohexanoic acid using CNBr as a spacer, | 13.36 |
| p-Aminobenzamidine using DADPA as a spacer | None (the column was stacked) |
| p-Aminobenzamidine using Epoxy as a spacer | 19.78 |
| Arginine using DADPA as a spacer | 6.04* |
| TEA (high conc.) using CNBr as a spacer | 0 |
| TEA (low conc.) using CNBr as a spacer | 0 |
| Arginine (low conc.) using CNBr as a spacer | 23.25 |
| Arginine (low conc.) using Epoxy as a spacer | 0 |
| Arginine (high conc.) using Epoxy as a spacer | 5.61 |

*This data point is the average of three runs.

The above table shows that the best ligands to remove plasmin(ogen) from the cryoprecipitate contained affinity gels that were robust enough to hold the sequence on loading, washings and elution without collapsing or gels which retained more than 50% of the loaded fibrinogen.

Table 3 illustrates both the efficiency of various gel types in the plasmin(ogen) removal and their capacity to retain fibrinogen in a concentrated cryoprecipitate.

Residual plasmin(ogen) present in the cryoprecipitate was adsorbed by the resins while fibrinogen was not, thus rendering the resulting supernatant essentially plasmin(ogen) free.

The fibrinogen content was measured by a clotting time test while the plasmin(ogen) content was measured by chromogenic assay.

Calculated recoveries of plasmin(ogen) and fibrinogen from lysine gels served as a golden standard for all other gel ligands used. The results, presented in table 2, indicate that only TEA ligands with epoxy spacer provided excellent removal of plasmin(ogen) and high Fibrinogen recovery (see table 3).

The high concentration of immobilized TEA provided a superior removal of plasmin(ogen) and similar recoveries of fibrinogen as compared to lysine bound ligand: recoveries of 89% versus 92% for fibrinogen and 89% versus 56% for plasmin(ogen) removal, respectively. All other resins were much less efficient in either removal of plasmin(ogen) or recovery of fibrinogen.

TABLE 3

Summary of the data obtained on fibrinogen recoveries and plasmin(ogen) removal in the unbound material using different immobilized ligands with BN1 buffer.

| Immobilized Ligands | Plasmin(ogen) removal (%) | Fibrinogen recovery (%) |
|---|---|---|
| Lysine using Epoxy as a spacer | 56* | 92* |
| TEA using DADP as a spacer | 49 | 84 |
| TEA (low conc.) using Epoxy as a spacer | 44.35 | 88.62 |
| TEA (high conc.) using Epoxy as a spacer | 89 | 89 |
| Arginine (high conc.) using CNBr as a spacer | 91.26 | 49 |

*This data point is the average of three runs.

EXAMPLE 3

Effect of Buffer Phosphate and BN1 on the Affinity Chromatography Profile of Lysine and TEA-Immobilized Resin Cryoprecipitate was treated with aluminium hydroxide to adsorb the Vitamin K dependent clotting factors, and then incubated with a solvent detergent mixture (SD-1% Tri(n-butyl)phosphate, 1% Triton X-100) for 4 hours at 30° C. to inactivate lipid enveloped viruses. The SD reagents were removed by castor oil extraction and hydrophobic interaction chromatography, and the preparation was subsequently pasteurized (10 h at 60° C.) in the presence of sucrose and glycine as stabilizers.

After pasteurisation, the sucrose and glycine were removed by diafiltration. Tranexamic acid (TEA) and Arginine hydrochloride were added as stabilizers prior to sterile filtration. Aliquots of the stabilized product was kept at −30° C. until used.

Aliquots of frozen, virus inactivated cryoprecipitate were thawed at 37° C. and dialyzed against buffer BN1 (composed of 0.12 M NaCl, 0.01 M Tri Na-citrate, 1 mM $CaCl_2$, at pH 7.0) or alternatively against 25 mM phosphate buffer. The latter solution was filtered through a 5 μm depth filter to give a clear solution.

A column of 10 mm in diameter (Biorad, USA) was packed with either 6 ml (wet volume) of immobilized TEA (TEA Sepharose 6B) or immobilized Lysine (Ceramic HyperDF/

Sepharose 4B) and washed with 4 volumes of each of the following solutions in sequence: i) purified water, ii) 1M NaCl, iii) purified water, iv) TLN 0.1 buffer (0.1 M NaCl, Lysine 0.02 M, Tris 0.05 M pH 9.0), v) TLN 1 buffer (1 M NaCl, Lysine 0.02 M, Tris 0.05 M pH 9) and vi) purified water. Equilibration was carried out with 4 volumes of BN1 or alternatively with phosphate buffer. The filtered cryoprecipitate was loaded into the column at a flow rate of 100 µl/min.

Samples of the unbound material were collected in plastic tubes and the resin washed with 16 column volumes of either BN1 buffer or phosphate buffer. Elution of plasmin(ogen) was carried out with TLN 1 buffer followed by washing with four volumes of 3 M NaCl solution, four volumes of purified water and four volumes of 25% ethanol supplemented with 1 M NaCl.

Table 4 illustrates the effectiveness of plasmin(ogen) removal by different kinds of resins and the recovery of fibrinogen. The fibrinogen content was measured by the clotting time assay (Clauss assay) while the plasmin(ogen) content was measured by a chromogenic assay.

Comparison between the different resins indicates that 95.4% to 96.4% of the fibrinogen content is retained in the unbound peak when the BN1 buffer is used. By contrast, fibrinogen recovery was low when phosphate buffer was used. Surprisingly, only the immobilized TEA resin provided both high removal of plasmin(ogen) and high recovery of fibrinogen.

Results with Lysine resin also demonstrated the improved efficiency with the BN1 buffer as compared to phosphate buffer.

TABLE 4

Summary of the data obtained by testing fibrinogen and plasmin(ogen) recoveries using immobilized resins with either BN1 buffer or phosphate buffer.

| Immobilized Ligands | Plasmin(ogen) removal (%) | Fibrinogen recovery (%) |
|---|---|---|
| TEA (high conc.) Epoxy + BN1 buffer | 77.1 | 96.4 |
| Lysine-Epoxy + BN1 buffer | 68.87 | 95.4 |
| Lysine-Epoxy + Phosphate buffer | 100 | 66.9 |
| Lysine CNBr + BN1 buffer | 62.5 | 121.8 |
| Lysine CNBr + Phosphate buffer | 100 | 62.2 |

EXAMPLE 4

Aliquots of frozen, virus inactivated cryoprecipitate were thawed at 37° C. and dialyzed against buffer BN1 (0.12 M NaCl, 0.01 M Tri Na-citrate, 1 mM $CaCl_2$ at pH 7.0) or alternatively against 25 mM phosphate buffer. The latter solution was filtered through a 5 µm depth filter to remove the insolubles.

A column of 26 mm in diameter (Pharmacia, Sweden) was packed with 50 ml (wet volume) of immobilized TEA (TEA Sepharose 6B) and washed with 4 volumes of purified water and the same volume of TLN 0.1 buffer (0.1 M NaCl, Lysine 0.02 M, Tris 0.05 M pH 9.0), TLN 1 buffer (1 M NaCl, Lysine 0.02 M, Tris 0.05 M pH 9) and purified water. Equilibration was carried out with 4 volumes of BN1 buffer (NaCl, Tri Na-citrate, $CaCl_2$, pH 7.0) and the filtered BAC was passed through the column at a flow rate of 700 µl/ml.

Samples of the unbound material were collected in a plastic dish and the resin was washed with at least 3 gel volumes of BN1 buffer. Elution of plasmin(ogen) was carried out with TLN 1 buffer following by washing with 3 M NaCl.

The unbound fractions from two runs were pooled and kept at 4° C. until concentration. Finally, the BAC was concentrated to about the original volume by diafiltration using a 100 cut-off membrane and against buffer BI (Glycine, NaCl, Tri Na-citrate, $CaCl_2$, pH 7) followed by filtration through 0.45 µm filter. 2% of arginine was added to the filtrate.

For stability tests, the resulting product was sterile filtered through 0.2 µm filter.

As indicated in table 5 using a larger and longer column improved the effectiveness of the TEA ligand, the recovery of fibrinogen was 100% and removal of plasmin(ogen) was below the detectable level of the plasmin(ogen) chromogenic assay.

Comparison between the product before and after diafiltration revealed a loss of 33% of the fibrinogen content. This phenomenon can be explained by technique problems which are discovered only within a small scale. Immobilised TEA resin provided, undoubtedly, both excellent removal of plasmin(ogen) and excellent recovery of fibrinogen.

TABLE 5

Summary of the data obtained by testing Fibrinogen and plasmin(ogen) recoveries in the unbound peak.

| Sample | Fibrinogen Recovery (%) | Plasmin(ogen) Recovery (%) |
|---|---|---|
| After loading | 100 | 0 |
| After loading and diafiltration | 66.2 | 0* |

Each data point is the average of two runs.
*The recovery of plasmin(ogen) after the pooled sample was concentrated 3.7 fold.

No residual TEA was found in both the eluted protein solution and the concentrated ultrafiltrated product. Analysis of the residual level of Tranexamic acid was done by HPLC.

Four additional runs were done, for removal of plasmin (ogen), using the same resin and running conditions as already described above (example 4). In general, the results of all of the samples examined were similar to the first results shown above.

No residual TEA was found in both the eluted protein solution of the concentrated ultrafiltrated product. Analysis of the residual level of Tranexamic acid was done by HPLC.

No adhesions were observed with either strips before removal of plasmin(ogen) or after it as was examined in a rat model.

The cryoprecipitate before and after removal of plasmin (ogen) was tested for degradation while incubated at room temperature. Data on the percentage of clottable proteins (by UV absorbance) on different samples is provided in Table 6.

TABLE 6

Percentage of clottable protein after incubation at room temperature of double viral inactivated, concentrated cryoprecipitate before and after removal of plasminogen by Epoxy Sheparose 6B ligated to tranexamic acid

| | Incubation time (weeks) | | | | | | |
|---|---|---|---|---|---|---|---|
| | 0 | 1 | 2 | 3 | 4 | 5 | 6 |
| Before treatment | 62.91 | 0 | 0 | 0 | 0 | 0 | 0 |
| After treatment | 73.44 | 70.80 | 68.24 | 65.69 | 63.69 | 63.84 | 62.46 |

Stability tests were done with strips which were prepared from cryoprecipitate before and after plasmin(ogen) removal followed by incubation at 37° C. in the presence of buffer. These strips were treated by the addition or omission of glycine and or arginine the results are summarized in Table 7 below.

TABLE 7

Degradation time in strips before and after plasmin(ogen) removal.

| Formulation | Strips degradation time (days) | | | | | | |
|---|---|---|---|---|---|---|---|
| | 0 | 1 | 2 | 3 | 4 | 5 | 6 |
| Before treatment | +++ | | | | | | |
| Before treatment + 2% arginine | +++ | – | – | – | – | – | – |
| Before treatment + 2% arginine + 1% glycine | +++ | – | – | – | – | – | – |
| After treatment | +++ | +++ | +++ | +++ | +++ | +++ | – |
| After treatment + 2% arginine + 1% glycine | +++ | +++ | +++ | +++ | +++ | +++ | – |

+++ This data point means existente of the strip
– This data point means degradation of the strip 1. The studies described in the following examples were performed on cryo-depleted, pooled fresh frozen plasma from normal, healthy donors. Due to the high concentration of antiplasmin and the small amount of plasmin in normal healthy donors (1), plasmin cannot be detected by a functional (chromogenic) assay (Schreiber A D, Kaplan A P, Austen K F. Plasma inhibitors of the components of the fibrinolytic pathway in man. 3. Clin. Invest 52: 1394-1401, 1973). Consequently, it is impossible to demonstrate the removal, purification and recovery from a TEA resin of plasmin from healthy donor plasma samples. However, a commercial ELISA kit for the detection of very low amounts of glu-plasmin(ogen) and, as found in previous studies, the TEA resin has equal affinity for both forms of plasmin(ogen) as well as for plasmin (Fredenburgh J P, Nesheim M E. Lys-plasmin(ogen) is a significant intermediate in the activation of Glu-plasmin(ogen) during fibrinolysis in vitro. 3 Biol Chem 267. 26150-6. 1992 and Miyashita C, Wenzel E., Heiden M. Plasmin(ogen): a brief introduction into ist biochemistry and function. Haemostasis 1:7-13, 1988.)
2. Thus the measurement of glu-plasmin(ogen) can be used as an indicator of the total plasmin(ogen) in the plasma.

EXAMPLE 5

Chromatographic Step

Studies were performed to determine the efficiency of an immobilized TEA on Sepharose 4FF in removing plasmin (ogen) from cryo-depleted Fresh Frozen Plasma (FFP) containing 1 IU/ml of plasmin(ogen). Aliquots of cryo-depleted fresh frozen plasma were thawed at 37° C. and filtered through a 3 μm depth filter to remove insoluble proteins.

A column of 10 mm in diameter (Pharmacia, Sweden) was packed with 2 ml (wet volume) of immobilized TEA and washed with 4 volumes of purified water and the same volume of TLN-0.1 buffer (0.1M NaCl, Lysine 0.02M, Tris 0.05M pH 9.0), TLN-1 buffer (1M NaCl, Lysine 0.02M, Tris 0.05M pH 9.0) and purified water. Equilibration was carried out with 4 volumes of BN1 buffer (0.12M NaCl, 0.01M Tri Na-citrate, 1 mM $CaCl_2$, pH 7.0) and the filtered plasma (~20 IU of plasmin(ogen)) was passed through the column at a flow rate of 1 ml/min.

The flow-through material was collected and frozen in a plastic bottle and the resin washed with at least 3 column volumes of BN1 buffer. Elution of plasmin(ogen) was carried out with TLN-1 buffer followed by washing with approximately three volumenes of 3M NaCl-solution, two volumes of purified water and two volumes of 20% ethanol+1 M NaCl (Method 1). In the second method (Method 2), the same procedure as that used for Method 1 was performed, but with an additional washing with 3 M NaCl before plasmin(ogen) elution.

Analytical Assays

Glu-Plasmin(ogen) Detection Assay:

The Imunclone® Glu-plasmin(ogen) ELISA kit (American Diagnostica, Greenwich, Conn., USA) used in these experiments is an enzyme-linked sandwich immunoassay specific for the determination of native human glu-plasmin (ogen) levels. The quantitation limit of the assay (according to the lowest calibration curve standard) in plasma or in plasma derivatives is 0.063 μg/ml.

Plasmin Activity:

a fibrinolytic assay was performed to semi-quantify plasmin activity in the eluates. Briefly, plasmin(ogen) free-fibrinogen (Enzyme Research) was incubated with various concentrations of normal pooled plasma (Unicalibrator, Stago) or purified plasmin(ogen) eluted from the affinity columns, in the presence of excess streptokinase. The time at which de degradation of the clot was complete was recorded and compared with the complete clot degradation of the sample.

Determination of the Protein:

Total protein was assayed using the Bradford method (Bradford M M. A rapid and sensitive method for the quantitation of microgram quantities of protein utilizing the principle of protein-dye binding. Anal Biochem. 72:248-54, 1976). Tables 8a and b show the results of chromatographic removal and purification of human plasma Glu-plasmin (ogen) by the TEA ligand. Table 8a summarizes the data obtained on the purification of plasmin(ogen). The table shows that method 2 resulted in a slightly better purification of plasmin(ogen) than method 1, with a purification of 567-fold and a yield of 91.6%. Table 8b shows that an average of 99.5% of plasmin(ogen) was removed from the unbound fraction, mostly accounted for by the amount recovered in the eluate (table 8a).

TABLE 8a

Effect of additional washing of TEA resin with 3M sodium chloride (Method 1 vs Method 2) on the specific activity, purification and recovery of plasmin(ogen) from plasma.

| Fraction | Method 1 Starting Material | Method 1 Eluate | Method 2 Starting Material | Method 2 Eluate |
|---|---|---|---|---|
| Volume (ml) | 40 | 13.2 | 40 | 20 |
| Protein (mg/ml) | 46.96 | 0.291 | 55.41 | 0.180 |
| Glu-plasmin(ogen) (μg/ml) | 65.4 | 18.2 | 78.0 | 142.9 |
| Plasmin(ogen) (IU/ml) | not done | | ~0.5 | ~1 |
| Specific Activity (mg plasmin(ogen)/mg protein) | 0.0014 | 0.625 | 0.0014 | 0.794 |
| Purification factor | | 446 | | 567 |
| Recovery of Plasmin(ogen) % | | 91.8 | | 91.6 |

TABLE 8b

Plasmin(ogen) removal from plasma
(mean of results for two methods)*

| Method | Chromato-graphic fraction | Glu-Plasmin(ogen) (average, μg/ml) | Volume (average, ml) | Plasmin(ogen) Removal (%) |
|---|---|---|---|---|
| 1 & 2* | Plasma | 71.7 | 40.0 | 99.5 |
|  | Unbound fraction | 0.18 | 83.5 |  |

*Methods 1 and 2 are identical up to and including collection of the unbound (flow-through) fraction.

EXAMPLE 6

Effect of Chromatographic Conditions on the Effectiveness of an Immobilized-Lysine Ligand in the Affinity Purification of Plasmin(ogen)

Chromatographic Step:

Affinity purification using a resin with an immobilized-lysine ligand was investigated using two commercially available lysine resins. A chromatographic method documented in the literature was used (see Robbins K C, Summaria L. Plasminogen and Plasmin. Methods Enzymol. 45: 257-73, 1976. for Method 2 described below) and also a method developed in the inventors' laboratory (Method 1 below).

Two immobilized Lysine resins (ceramic HyperDF produced by Biosepra and Sepharose 4B manufactured by Pharmacia) were each packed into columns of 10 mm diameter (Pharmacia, Sweden). Each column contained 2 ml (wet volume) of resin.

Aliquots of cryo depleted fresh frozen plasma were thawed at 37° C. and were filtered through a 3 μm depth filter to give a clear solution.

The chromatographic step was performed using one of the following methods:

Method 1

The column was washed with 4 volumes of each of the following solutions: 1) purified water, 2) TLN-0.1 3) TLN-1 and 4) purified water. Equilibration was carried out with 4 volumes of BN1. The filtered plasma (40 ml) was loaded onto the column at a flow rate of 1 ml/min. Samples of the flow through material were collected in plastic bottles and the resin was washed with BN1 buffer. Elution of plasmin(ogen) was carried out with TLN-1 buffer followed by washing with 3 M NaCl solution, 2 volumes of purified water and 2 volumes of 20% ethanol+1 M NaCl.

Method 2: (ref. 5)

Aliquots of cryo depleted fresh frozen plasma (40 ml) were filtered through a 3 μm depth filter. 4 ml of 0.5M Tris, 0.2M lysine, 1M NaCl buffer, pH 9 were added to 40 ml filtered plasma.

The column was washed with 4 column volumes of purified water and equilibrated with 0.1 M phosphate buffer, pH 7.4. The diluted plasma was passed through the resin at a flow rate of 1 ml/min. Samples of the unbound material were collected in plastic bottles and the resin was washed with 0.1M phosphate buffer, pH 7.4 until the absorbance of the effluent at 280 nm reached baseline. The plasmin(ogen) was then eluted with 0.2M ε-amino-caproic acid dissolved in 0.1M phosphate buffer, pH 7.4 and collected in a plastic dish. The elution was followed by washing with approximately 2 volumes of 3 M NaCl solution and purified water.

Tables 9a and 9b compare the removal and purification of plasmin(ogen) by two different commercially available immobilized-lysine resins using two different purification methods with each. Although there is relatively little difference in the recovery of plasmin(ogen) in the eluates (9a), it can be seen that by using method 2 and the resin Ceramic HyperDF, a much higher purification of plasmin(ogen) is achieved.

The results show that using Lys-ceramic Hyper DF resin and chromatographic method 2, a 444-fold purification was achieved. In addition, most of the plasmin(ogen) in the starting material was recovered in the peak fractions (76.5% in the unbound fraction+10.9% in the eluate, with only about 10% of the loaded plasmin(ogen) unaccounted for). However, the plasmin(ogen) removal from the unbound fraction was only 23.5%.

TABLE 9a

Specific activity, purification factor and recovery from plasma of plasmin(ogen) using two different commercially available immobilized-lysine resins and two different chromatographic methods.

|  | Method 1 | | | Method 2 | | |
|---|---|---|---|---|---|---|
|  |  | Eluate | | | Eluate | |
| Fraction | Load | Ceramic Hyper DF | Sepharose 4B | Load | Ceramic Hyper DF | Sepharose 4B |
| Volume (ml) | 40 | 8.1 | 7.2 | 40 | 8.2 | 9.8 |
| Protein (mg/ml) | 55.94 | 0.347 | 0.345 | 60.05 | 0.0719 | 0.672 |
| Glu-plasminogen (μg/ml) | 65.4 | 40.3 | 41.9 | 60.8 | 32.2 | 19.9 |
| Specific Activity (mg plasminogen/mg protein) | 0.0012 | 0.116 | 0.121 | 0.001 | 0.444 | 0.030 |
| Purification factor |  | 97 | 101 |  | 444 | 30 |
| Recovery (%) |  | 12.5 | 11.6 |  | 10.9 | 8.2 |

TABLE 9b

Plasmin(ogen) removal in the unbound peaks for both methods

| Method | Resin used | Chromato-graphic fraction | Volume (ml) | Glu-plasmin-(ogen) μg/ml | Total Glu-plasmin-(ogen) (μg) | Plasmin-(ogen) Removal (%)* |
|---|---|---|---|---|---|---|
| 1 | Ceramic Hyper DF | Plasma | 40 | 65.4 | 2616 | 54.6 (45.4) |
|  |  | Unbound | 72 | 16.5 | 1188 |  |
|  | Sepharose | Plasma | 40 | 65.4 | 2616 | 58.0 |

TABLE 9b-continued

Plasmin(ogen) removal in the unbound peaks for both methods

| Method | Resin used | Chromato-graphic fraction | Volume (ml) | Glu-plasmin-(ogen) μg/ml | Total Glu-plasmin-(ogen) (μg) | Plasmin-(ogen) Removal (%)* |
|---|---|---|---|---|---|---|
| | 4B | | | | | (42.0) |
| | | Unbound | 82 | 13.4 | 1099 | |
| 2 | Ceramic Hyper DF | Plasma | 40 | 60.8 | 2432 | 23.5 (76.5) |
| | | Unbound | 89 | 20.9 | 1860 | |
| | Sepharose 4B | Plasma | 40 | 60.8 | 2432 | 33.0 (67.0) |
| | | Unbound | 91 | 17.9 | 1629 | |

*The values in brackets represent the plasminogen recoveries in the unbound peak.

The invention claimed is:

1. A method for specifically removing or isolating plasminogen or plasmin from a mixture plasma derived cryoprecipitate containing plasminogen or plasmin in the presence of fibrinogen and fibronectin comprising
contacting the plasma derived cryoprecipitate with an amino acid having a rigid constitution, wherein the distance between the amino group and the carboxylic group of the amino acid is kept substantially constant by the rigid constitution of the amino acid, wherein the amino group of the amino acid and the carboxylic group of the amino acid are about 6-8 Angstroms apart, and wherein the amino acid is covalently bound to a support via the amino group of the amino acid, such that the plasminogen or plasmin binds to amino acid bound to the support, followed by
separating the support-bound plasminogen or plasmin from the plasma derived cryoprecipitate.

2. The method according to claim 1 wherein the amino group and the carboxylic group of the amino acid are about 7 Angstroms apart.

3. The method according to claim 1 wherein the support is a chromatographic material.

4. The method according to claim 3 wherein the chromatographic material is a hydrophilic material, controlled pore glass, silica gel, dextran, or an organic artificial polymer.

5. The method according to claim 3 wherein the chromatographic material is agarose, cellulose, or an organic artificial polymer based on polyacrylamide polystyrene.

6. The method according to claim 3 wherein the chromatographic material is agarose or sepharose.

7. The method according to claim 3 wherein the chromatographic material is a particulate material or a monolithic block-material.

8. The method according to claim 1 wherein the rigid amino acid is tranexamic acid bound to the support via a linker between the support and the tranexamic acid.

9. The method according to claim 8 wherein the linker is a bifunctional linker.

10. The method according to claim 9 wherein the bifunctional linker is N-hydroxy succinimide, di-arachidonyl phosphatidic acid, cyanogen bromide, epoxy, diaminodipropylamine (DADPA), 1,6 diaminohexane, succinic acid, 1,3 diamino-2-propanol, ethylendiamine (EDA), 5-thio-2-nitrobenzoic acid, pyridyldisulfide, iodoacetamide, a maleimide activated support, or combination thereof.

11. The method of claim 10 wherein the rigid amino acid is 4-aminomethylbicyclo-[2.2.2.]-octane-1-carboxylic acid.

12. The method according to claim 8 further comprising, after contacting the plasma derived cryoprecipitate with the support having bound tranexamic acid, (i) incubating the plasma derived cryoprecipitate with the support for a sufficient time period to bind plasminogen or plasmin and (ii) eluting with a neutral aqueous solution containing sodium salts, calcium salts, and buffer salts.

13. The method according to claim 1 wherein the support is modified by a moiety which reacts with primary or secondary amino groups.

14. The method according to claim 1 further comprising, after contacting the plasma derived cryoprecipitate with the support-bound amino acid plasmin or plasminogen, eluting with an aqueous solution containing a sufficient amount of a ligand competing with the plasmin or plasminogen on the binding sites of the support-bound amino acid.

15. The method of claim 14, wherein the ligand is lysine.

16. The method according to claim 1 wherein the rigid amino acid is 4-aminomethylbicyclo-[2.2.2.]-octane-1-carboxylic acid (EMBOCA).

* * * * *